United States Patent [19]

Cook et al.

[11] Patent Number: 5,387,713
[45] Date of Patent: Feb. 7, 1995

[54] PROCESS FOR PURIFICATION OF CARBOXYLIC ACIDS

[75] Inventors: John Cook, Hull; Ruth A. Hazel; Peter J. Wilson, both of North Humbershire, England

[73] Assignee: BP Chemicals Limited, London, England

[21] Appl. No.: 805,373

[22] Filed: Dec. 11, 1991

[30] Foreign Application Priority Data

Jan. 5, 1991 [GB] United Kingdom ............... 9100216

[51] Int. Cl.⁶ .............................................. C07C 51/42
[52] U.S. Cl. .................................................. 562/608
[58] Field of Search ........................................ 562/608

[56] References Cited

U.S. PATENT DOCUMENTS

| 2,273,459 | 11/1938 | Britton | 562/608 |
|---|---|---|---|
| 2,286,995 | 8/1939 | Reichert | 562/608 |
| 2,352,253 | 6/1944 | Cockerille | 562/898 |
| 2,504,195 | 4/1950 | Hall et al. | 203/77 |
| 3,546,284 | 12/1970 | List et al. | 562/482 |
| 3,551,300 | 12/1970 | Longley | 203/31 |
| 3,772,156 | 11/1973 | Johnson et al. | 203/30 |
| 4,149,013 | 4/1979 | Klein | 562/593 |
| 4,338,260 | 7/1982 | Schirmann | 260/502 |
| 4,459,240 | 7/1984 | Pralus et al. | 260/502 |
| 4,549,025 | 10/1985 | Delcanale et al. | 546/327 |
| 5,144,067 | 9/1992 | Zoeller et al. | 562/479 |

FOREIGN PATENT DOCUMENTS

| 1138891 | 1/1983 | Canada . |
|---|---|---|
| 1279656 | 1/1991 | Canada . |
| 13551 | 7/1980 | European Pat. Off. . |
| 0087870 | 9/1983 | European Pat. Off. . |
| 0217191 | 4/1987 | European Pat. Off. . |
| 0322215 | 6/1989 | European Pat. Off. . |
| 2940751 | 4/1980 | Germany . |
| 58-116436 | 7/1973 | Japan . |
| 48-30615 | 9/1973 | Japan . |
| 61-56151 | 3/1986 | Japan . |
| 2134342 | 2/1990 | Japan . |
| 372434 | 5/1932 | United Kingdom . |
| 749098 | 5/1956 | United Kingdom . |
| 1201260 | 8/1970 | United Kingdom . |
| 1233121 | 5/1971 | United Kingdom . |
| 1293774 | 10/1972 | United Kingdom . |
| 1360328 | 7/1974 | United Kingdom . |
| 1423485 | 2/1976 | United Kingdom . |
| 2033901 | 5/1980 | United Kingdom . |
| 292281 | 12/1968 | U.S.S.R. . |
| 1437363 | 11/1988 | U.S.S.R. . |
| 9203403 | 3/1992 | WIPO . |

OTHER PUBLICATIONS

Patent Abstracts of Japan, vol. 9, No. 301 (C-316) (2024) 28 Nov. 1985 & JP-A-60 139 641 (DAICEL) 24 Jul. 1985 *abstract*.

*Primary Examiner*—José G. Dees
*Assistant Examiner*—Joseph Conrad
*Attorney, Agent, or Firm*—Brooks Haidt Haffner & Delahunty

[57] ABSTRACT

Carboxylic acids produced by carbonylation and having iodide and oxidisable impurities are purified by contacting with hydrogen peroxide and recovering the purified acid by distillation or evaporation. Preferably a strong acid such as sulphuric acid is used as a catalyst. Product contamination by sulphur from sulphuric acid and by excess peroxide may be reduced by the use of metal salts in the recovery step.

15 Claims, No Drawings

PROCESS FOR PURIFICATION OF CARBOXYLIC ACIDS

The present invention relates to the purification of carboxylic acids and in particular to a process for removing iodide and oxdisable impurities from carboxylic acids, preferably acetic acid.

The liquid phase carbonylation of methanol is a well known industrially operated process and is widely operated commercially. The carbonylation process, which is typically catalysed by rhodium and methyl iodide, is described in detail in, for example, UK patent number GB 1233121. European patent application number EP 87870 describes a modification of this process in which acetic acid is coproduced with acetic anhydride, from mixtures of methanol, methyl acetate and water under anhydrous conditions.

A problem with acetic acid produced by processes such as those described in GB 1233121 and EP-A-87870 is that even after purification by conventional distillation it still contains oxidisable impurities and relatively large amounts (typically 100 ppb-2 ppm) of iodide impurities. For certain applications, e.g. in the subsequent conversion of the acetic acid into vinyl acetate, these impurities are detrimental and need to be removed.

UK patent GB 1201260 relates to purification of formic acid by treatment with hydrogen peroxide to reduce colour-forming impurities. Soviet patent number SU 1437363 relates to purification of acetic acid being regenerated in the production of cellulose acetates and acetic anhydride by treating with hydrogen peroxide in the presence of polyphosphoric acid or a salt thereof. Japanese laid open patent application number H2-134342 relates to decolourisation of acetic acid with hydrogen peroxide or percarboxylic acid. None of these publications addresses the problem of removing iodide impurities from carboxylic acids.

European patent publication number EP-A-0013551 relates to a process for removing iodine from organic compounds in which the compounds are treated at 50° to 200° C. with oxidising agents such as oxygen or hydrogen peroxide and the reaction mixture is brought into contact with an adsorption agent for example active carbon. The compounds envisaged for treatment are in particular the products of oxidative acylation of olefins. EP-A-0013551 does not describe purification of carboxylic acids produced by carbonylation to remove iodide and oxidisable impurities. EP-A-0013551 does not describe recovering purified carboxylic acid from hydrogen-peroxide-treated-acid by distillation or evaporation.

UK patent number GB 1293774 describes a process for the purification of carboxylic acids contaminated with trace amounts of halides by treating with an inorganic oxidising agent and subjecting the treated acid to distillation. According to GB 1293774, the oxidising agent contains an alkali metal and/or chromium or a metal of Groups VIIB of the periodic table according to Deming. The preferred treating agents contain sodium or potassium and manganese or chromium; potassium and sodium permanganate being especially preferred.

European patent number EP 0217191B describes a process for the separation of iodine and its compounds from the carbonylation products obtained in the carbonylation of dimethyl ether, methyl acetate or methanol. The process of EP 0217191B comprises treating the carbonylation products at temperatures of 20° C. to 200° C. with peracetic acid, diacetyl peroxide or compounds forming these under the reaction conditions and then separating the product by distillation. This is said to reduce iodine contents to less than 20 ppb in the carbonylation products.

Such processes are not entirely satisfactory. The problem to be solved therefore is to provide a process for removing iodide and oxidisable impurities from carboxylic acids which have been prepared by carbonylation.

Thus, according to the present invention there is provided a process for purifying impure carboxylic acid which has been prepared by the carbonylation of a suitable reactant in the presence of a carbonylation catalyst and an iodide promoter and which contains iodide and oxidisable impurities, which process comprises the steps of:

(a) contacting the impure carboxylic acid with hydrogen peroxide, and (b) recovering purified carboxylic acid from the product of step (a) by distillation or evaporation.

The process of the present invention is suitable for removing iodide and oxidisable impurities from carboxylic acids having up to 6 carbon atoms preferably acetic acid, propionic acid and/or butyric acids, more preferably acetic acid.

Processes for preparing carboxylic acids by carbonylation are known in the art. Suitably the acid is produced by the carbonylation of an alkyl ester of a carboxylic acid, an alkanol, an alkyl halide and/or a dialkyl ether in the presence of a Group VIII metal carbonylation catalyst, for example rhodium or iridium and in the presence of an iodide promoter. Acetic acid may be prepared by carbonylation of methanol, methyl acetate, methyl halide and/or dimethyl ether. Suitable processes for preparing acetic acid are described in GB 1233121 and EP-A-87870, the contents of which are hereby incorporated by reference. Suitably the carboxylic acid is separated from the carbonylation catalyst and iodide promoter by distillation and/or evaporation before purification by the process of the present invention. Distillation to remove the bulk of the iodide and/or oxidisable impurities prior to contacting with hydrogen peroxide may also be used depending upon the concentrations of the impurities.

The iodide impurities comprise iodine-containing compounds, for example, methyl iodide, butyl iodide, hexyl iodide and inorganic iodides, typically at 100 ppb to 2 ppm total iodine in the acid.

The exact nature of the oxidisable impurities is not known, but their presence causes the carboxylic acid to have a permaganate time of less than 2 hours and so fail the permaganate test as herein defined.

The process of the present invention can reduce iodide impurities from about 500 ppb to below 50 ppb and oxidisable impurities sufficiently for the carboxylic acid to pass the permanganate test.

The hydrogen peroxide is used as an aqueous solution, preferably at 50-60% w/v.

The amount of hydrogen peroxide used will depend upon the amount of iodide and oxidisable impurities in the carboxylic acid but will generally be in the range 10 to 10000 ppm by weight of the impure carboxylic acid, preferably 100 to 5000 ppm.

Preferably, the impure carboxylic acid is contacted with hydrogen peroxide in the presence of a strong acid. Suitable strong acids for use in the present invention comprise sulphuric acid, methane sulphonic acid, para-toluene sulphonic acid, trifluoroacetic acid, phosphoric acid and strong acid ion exchange resins such as Amberlyst 15. A preferred strong acid is sulphuric acid.

The strong acid may be used without dilution but conveniently may be used as a solution in the carboxylic acid. The amount of sulphuric acid used in step (a) may be in the range 10 to 1000 ppm.

The temperature at which step (a) is performed should be high enough to prevent the carboxylic acid freezing at one extreme or boiling at the other. The temperature will depend upon a number of factors. In particular, the higher the temperature the faster the reaction between the hydrogen peroxide and the impurities but also the faster it decomposes. Typically, for acetic acid, the temperature will be in the range 20° to 118° C. although higher temperatures may be used if the process is operated at superatmospheric pressure.

The step (a) of the process may be operated at subatmospheric, atmospheric or superatmospheric pressure, preferably atmospheric pressure.

The contact time of the impure carboxylic acid with the hydrogen peroxide will depend upon such factors as the concentration of impurities and reagents, and the temperature, but will generally be in the range 1 minute to 24 hours, preferably 10 minutes to 5 hours.

In step (b) the purified carboxylic acid is recovered by distillation or evaporation, preferably as a liquid side draw from a multistage fractional distillation column, with small heads and base bleeds. A residues concentrator may be used on the base bleed from the distillation column to reduce the volume of residues, with return of acid to the distillation column.

It is possible to perform steps (a) and (b) together by adding the hydrogen peroxide and optional strong acid to a distillation column. Preferably the steps may be performed separately in sequence rather than simultaneously.

The process of the present invention may be performed as a batch or continuous process. A batch process generally produces better quality product acid but on an industrial scale a continuous process is generally preferred.

When sulphuric acid is used as the strong acid in step (a) the separated carboxylic acid in step (b) may contain sulphur impurities. Contamination of the purified carboxylic acid by these sulphur impurities may be reduced by the use of a suitable metal salt in the distillation/evaporation step (b). Suitable metal salts are carboxylate salts such as acetate salts and/or are nitrate salts, for example potassium, silver and/or calcium carboxylate e.g. acetate and/or nitrate. Suitable salts are also potassium and/or magnesium hydroxide and/or copper (I) oxide. Carboxylate salts may be added to step (b) as such or may be formed in situ by the addition of hydroxides. Preferred salts are potassium carboxylate, particularly acetate and silver nitrate. More than one salt may be used. Suitably the metal salt is present at from about 1% w/w to about 10% w/w, preferably from about 1% w/w to about 7% w/w in the kettle/reboiler of the step (b) distillation column.

Contamination of the purified carboxylic acid by excess peroxide may be reduced by the use of a suitable metal salt in the distillation/evaporation step (b). Suitable metals salts are salts of the carboxylic acid for example carboxylate salts of potassium, silver and/or calcium. Suitable metal salts are also salts such as potassium and/or magnesium hydroxide and/or copper (I) oxide. Carboxylate salts may be added to step (b) as such or may be formed in situ by the addition of hydroxide salts. A preferred metal salt is potassium carboxylate, particularly potassium acetate. More than one salt may be used. Suitably the metal salt is present at from about 1% w/w to about 15% w/w, preferably about 1% w/w to about 10% w/w in the kettle/reboiler of the step (b) distillation column/evaporator. The metal salts used to reduce peroxide carryover may also be used to reduce sulphur carryover if sulphuric acid is used in step (a).

The invention will now be illustrated by reference to the following examples.

In the examples iodide impurities were measured by neutron activation analysis. The permanganate times were measured at room temperature by adding 0.1 ml of 0.02M potassium permanganate to 2 ml of sample and 10 ml of distilled water; the permanganate time being the time required for the pink colour of the permanganate to be discharged. A permanganate time of greater than 2 hours was taken as a pass of the test. Water concentrations were determined by automatic Karl Fischer titration. Sulphur contents were determined by X-ray diffraction (XRF) with a limit of detection of 2 ppm. Samples with very low (ppb) levels of iodide impurities were analysed for sulphur content by microcoulormetry down to 0.2 ppm.

Continuous Treatment Experiments

Continuous treatment of impure acetic acid prepared by carbonylation was studied using a heated stirred treater vessel from which liquid product was passed to the reboiler of a 12 actual stage distillation column. The distillation column had a purified acid liquid product take-off at stage 4 counted from the base of the column. The distillation column had a pumped heads reflux and small head and base take-off bleeds.

The results of treatment with and without sulphuric acid are

TABLE 1

| | | Purification of Acetic Acid According to the Present Invention | | | | | | |
|---|---|---|---|---|---|---|---|---|
| | | Impure Acetic Acid | | | | | Product Acetic Acid | |
| Experiment No. | Reference | Peranganate Time (mins) | Iodide Impurities | Treatment Reagents | Temp. °C. | Time hour | Permanganate Time | Iodide Impurities (ppb) | Sulphur (ppm) |
| 1 | AC4/15 | 20 | ca 2 ppm | 1000 ppm $H_2O_2$ | 115 | 1 | 2–3 hours | 137 | — |
| 2 | AC4/13 | 20 | ca 2 ppm | 500 ppm $H_2O_2$ | 115 | 1 | 1 hr 50 mins | 228 | — |
| 3 | AC4/12 | 20 | ca 2 ppm | 250 ppm $H_2O_2$ | 115 | 1 | 1 hour | 309 | — |
| 4 | AC4/11 | 20 | ca 2 ppm | 100 ppm $H_2O_2$ | 115 | 1 | 0.5–1 hour | 258 | — |
| 5 | AC4/16B | 20 | ca 2 ppm | 500 ppm $H_2O_2$ | 75 | 1 | 0.5–1 hour | 265 | — |
| 6 | AC4/17 | 20 | ca 2 ppm | 500 ppm $H_2O_2$/250 ppm $H_2SO_4$ | 115 | 1 | >24 hours | 94 | — |
| 7 | AC4/27 | 70 | 695 ppb | 250 ppm $H_2O_2$/50 ppm $H_2SO_4$ | 115 | 1 | >6 hours | 45 | <2 |
| 8 | AC4/34 | 10 | 224 ppb | 500 ppm $H_2O_2$/50 ppm $H_2SO_4$ | 115 | 1 | 17 hours | 27 | — | given in Table 1. Referring to Table 1, it will be seen that treatment with 1000 ppm hydrogen peroxide alone at 115° C. produces acid which passes the permanganate test. Table 1 also shows the benefits of using a strong acid such as sulphuric acid. Thus referring to Table 1 it will be seen that treating impure acetic acid with 500 ppm hydrogen peroxide reduces iodide impurity levels from about 2 ppm to 230 ppb. If 250 ppm sulphuric acid is added to the 500 ppm hydrogen peroxide treatment the level of iodide impurities is further reduced to 94 ppb, comparable with that obtained using 1000 ppm hydrogen peroxide alone. The permanganate time is also improved by the addition of sulphuric acid. Extended operation with sulphuric acid feed to the treater and with a residue concentrator taking residue from the distillation column base bleed and returning acid to the distillation column, resulted in an increase in sulphur impurities in the purified acid.

To show that treatment of impure acetic acid with hydrogen peroxide and sulphuric acid is different from treatment with peracetic acid, comparative experiments A-D were performed using different levels of peracetic acid in place of hydrogen peroxide/sulphuric acid and the results are shown in Table 2. For impure acetic acid containing 224 ppb iodide impurities comparison of experiment AC4/34 in Table 1 with comparison experiment AC4/43 in Table 2 shows, that although 500 ppm hydrogen peroxide has a comparable active oxygen content to 1120 ppm peracetic acid, the presence of 50 ppm sulphuric acid causes a significant improvement in the permanganate time of the treated acid to 17 hours, compared to 2 hours for acid treated with 1140 ppm peracetic acid.

Batch Experiments

In batch experiments, acetic acid prepared by carbonylation was heated in a flask to 115° C. before the treatment reagents were added via a syringe directly into the liquid. The mixture was then heated for 1 hour before 85% of the acid was distilled from the flask and analysed. A series of batch experiments were performed using different strong acids. The results are given in Table 3. Referring to Table 3 it will be seen by comparison of Experiment 9

TABLE 3-continued

| Experiment No. | Treatment | Product Acetic Acid Permanganate Time (hours) |
|---|---|---|
| Comp. P | 140 ppm $H_2O_2$ 1% acetic anhydride | 2.3 |

MSA = Methane sulphonic acid
TFA = Trifluoroacetic acid
Amberlyst 15 = strong acid ion exchange resin with Experiment 2 in Table 1 that a batch process produces a better quality product than does a continuous process.

Additives to Reduce Sulphur Impurities

A series of batch experiments were performed by batch distilling the reboiler contents from a continuous treatment distillation column or a solution prepared to simulate such contents by heating together acetic acid, hydrogen peroxide and sulphuric acid. The batch distillations were performed in the absence and presence of various metal salts. Kettle and distillate fractions were analysed for sulphur content during the distillation and the results are shown in Tables 4(a) to (f). The results show all the salts tested, potassium acetate, silver nitrate, calcium nitrate, magnesium hydroxide and copper (I) oxide to be effective in reducing sulphur contamination of the purified acid.

Two continuous experiments were performed using the previously described continuous treatment apparatus. Impure acetic acid containing 224 ppb iodide and having a permanganate time of 0.2 hour was treated at 115° C. with 500 ppm hydrogen peroxide and 50 ppm sulphuric acid in the treater with a residence time of 1 hour before being passed to the distillation column. A metal salt (75 ppm potassium acetate or 20 ppm silver nitrate) was added to the distillation column reboiler. The results are shown in Table 5. The iodide impurity removal in the presence of silver nitrate was marginally better than in the presence of potassium acetate. A solid (analysed by IR to be a sulphate salt) was found in the distillation column reboiler. The heads bleed from the distillation column contained less than 2 ppm sulphur when the salts were used.

TABLE 2

Comparative Experiment

| Comparative Experiment No. | Reference | Impure Acetic Acid | | Treatment | | | Product Acetic Acid | |
|---|---|---|---|---|---|---|---|---|
| | | Peranganate Time (mins) | Iodide Impurities (ppb) | Reagents | Temp. °C. | Time hours | Permanganate Time (mins) | Iodide Impurities (ppb) |
| A | AC4/43 | 10 | 224 | 1400 ppm $CH_3CO_3H$ | 115 | 2 | 120 | 30 |
| B | AC4/42 | 10 | 224 | 400 ppm $CH_3CO_3H$ | 115 | 2 | ca 40 | N/A |
| C | AC4/40 | 10 | 224 | 280 ppm $CH_3CO_3H$ | 115 | 2 | ca 20 | N/A |
| D | AC4/41 | 10 | 224 | 280 ppm $CH_3CO_3H$ | 100 | 2 | ca 20 | N/A |

TABLE 3

| Experiment No. | Treatment | Product Acetic Acid Permanganate Time (hours) |
|---|---|---|
| 9 | 500 ppm $H_2O_2$ | >6 |
| 10 | 140 ppm $H_2O_2$ | 2.5 |
| 11 | 140 ppm $H_2O_2$ 50 ppm $H_2SO_4$ | 9.5 |
| 12 | 140 ppm $H_2O_2$ 50 ppm $H_3PO_4$ | 2 |
| 13 | 140 ppm $H_2O_2$ 250 ppm $H_3PO_4$ | 6 |
| 14 | 70 ppm $H_2O_2$ | 0.7 |
| 15 | 70 ppm $H_2O_2$ 50 ppm MSA | 3.5 |
| 16 | 70 ppm $H_2O_2$ 50 ppm TFA | 0.8 |
| 17 | 70 ppm $H_2O_2$ 1% Amberlyst 15 | 1.5 |

TABLE 4

Batch Testing of Metal Salts to Reduce Sulphur Impurities

| Fraction | Sulphur in kettle ppm | Sulphur in Distillate Fraction ppm |
|---|---|---|
| (a) Experiment 18 - No Metal Salt | | |
| 3 | approx 350 | 2 |
| 6 | approx 570 | <2 |
| 9 | approx 850 | 2 |
| 12 | approx 1100 | 3 |
| 14 | 1710 | 11 |
| 18 | 4430 | 44 |
| 21 | 34000 | 550 |
| (b) Experiment 19 - 1% Potassium Acetate Added | | |

TABLE 4-continued

Batch Testing of Metal Salts to Reduce Sulphur Impurities

| Fraction | Sulphur in kettle ppm | Sulphur in Distillate Fraction ppm |
|---|---|---|
| 1 | 500 | <2 |
| 5 | 730 | <2 |
| 10 | 1250 | <2 |
| 14 | 2780 | <2 |
| 16 | 5290 | <2 |
| (c) Experiment 20 - 1% Silver Nitrate Added | | |
| 1 | 500 | 2 |
| 5 | 730 | 2 |
| 10 | 1600 | <2 |
| 12 | 3315 | <2 |
| 14 | 8825 | <2 |
| (d) Experiment 21 - 1% Calcium Nitrate Added | | |
| 1 | 500 | <2 |
| 5 | 730 | 2 |
| 10 | 1250 | 2 |
| 14 | 2780 | <2 |
| 16 | 5290 | 2 |
| (e) Experiment 22 - 1% Magnesium Hydroxide Added | | |
| 1 | 500 | <2 |
| 5 | 685 | <2 |
| 10 | 1080 | <2 |
| 14 | 2070 | <2 |
| 16 | 3965 | <2 |
| (f) Experiment 23 - 1% Copper I Oxide Added | | |
| 1 | 500 | 2 |
| 5 | 785 | 2 |
| 10 | 1900 | 2 |
| 12 | 4480 | 2 |

TABLE 5

Continuous Treatment - Addition of Metal Salts to Reduce Sulphur Impurities

| | | | | Product Acid | | |
|---|---|---|---|---|---|---|
| Run No. | Reboiler Feed | Reboiler Contents | Time on Stream/days | Permanganate Time (hours) | Total Iodide (ppb) | Sulphur (ppm) |
| 115 | 75 ppm KOAc | 3.5% KOAc | 1½ | >6 | 11 | N/A |
| | | | 4½ | >6 | 41 | N/A |
| | | | 7 | 6 | 14 | N/A |
| | | | 9 | 3½ | N/A | N/A |
| | | | 9½ | 6 | N/A | N/A |
| | | | 10½ | 3.5 | N/A | <0.2 |
| | | | 11 | 2.5 | N/A | <0.2 |
| | | | 11½ | 2.5 | 23 | <0.2 |
| | | | 13 | 5 | 16 | N/A |
| 115 RUN AVERAGES | | | — | about 6 | 16 | <0.2 |
| 116 | 20 ppm AgNO₃ | 1% AgNO₃ | 1 | >7 | 2 | <0.3 |
| | | | 3 | >6 | 5 | <0.3 |
| | | | 6½ | >5 | 13 | <0.3 |
| | | | 7½ | 6 | 12 | <0.3 |
| | | | 9 | >6 | 12 | <0.3 |
| | | | 11 | 5 | 16 | <0.3 |
| 116 RUN AVERAGES | | | — | about 6 | 11 | <0.3 |

Notes
(1) Treater conditions = Temperature = 115° C.
Residence time = 1 hour
H$_2$O$_2$ treatment = 500 ppm
H$_2$SO$_4$ treatment = 50 ppm
(2) The run averages reflect all the analytical data obtained over the operating period (only some of which is shown in the Table).
(3) Impure acetic acid feed = Total iodides by NAA = 224 ppb
Permanganate time = 0.2 hrs Additives to Reduce Excess Peroxide A batch experiment was performed to show that metal salts can be used to reduce excess peroxide after the treatment of impure carboxylic acid with hydrogen peroxide.

500 ml of acetic acid was batch treated with 500 ppm hydrogen peroxide and 50 ppm sulphuric acid at 115° C. for 1 hour. After this time the peroxide concentration was found to be 220 ppm (as hydrogen peroxide). 425 mls of the acid was then distilled off. The peroxide concentration of the distillate was 199 ppm.

An identical sample was treated in the same manner as above, where after 1 hour the peroxide concentration was 236 ppm. Potassium acetate was then added to the acetic acid to yield a total concentration of 7% w/w before 425 mls of distillate was collected, the peroxide concentration of which was 34 ppm.

It is envisaged that in a continuous process the metal salt would be added to the distillation/evaporation stage (b) to reduce excess peroxide carryover into the purified acid product. Such metal salts may also reduce sulphur carryover if sulphuric acid is used in step (a).

We claim:

1. In a carbonylation process wherein a suitable reactant is carbonylated in the presence of a carbonylation catalyst and an iodide promoter to produce carboxylic acid, a method for purifying impure carboxylic acid containing iodide and oxidisable impurities, wherein said method comprises the steps of: (a) contacting said impure carboxylic acid with hydrogen peroxide, and (b) recovering by distillation or evaporation from the product of step (a) purified carboxylic acid having a reduced content of iodide and oxidisable impurities.

2. A process as claimed in claim 1 in which said carboxylic acid has up to 6 carbon atoms.

3. A process as claimed in claim 2 in which said carboxylic acid comprises acetic acid.

4. A process as claimed in claim 1 in which step (a) is performed in the presence of a strong acid.

5. A process as claimed in claim 4 in which said strong acid comprises sulphuric acid.

6. A process as claimed in claim 5 in which step (b) is performed in the presence of a metal salt to reduce sulphur contamination of the purified carboxylic acid.

7. A process as claimed in claim 6 in which said metal salt comprises at least one salt selected from the group consisting of carboxylate and nitrate salts of potassium, calcium and silver.

8. A process as claimed in claim 7 in which said metal salt comprises potassium acetate.

9. A process as claimed in claim 6 in which said metal salt comprises at least one salt selected from the group consisting of potassium hydroxide, magnesium hydroxide and copper (I) oxide.

10. A process as claimed in claim 1 in which step (b) is performed in the presence of a metal salt to reduce peroxide contamination of the purified carboxylic acid.

11. A process as claimed in claim 10 in which said metal salt comprises at least one salt selected from the group consisting of carboxylate salts of potassium, silver and calcium.

12. A process as claimed in claim 11 in which said metal salt comprises potassium acetate.

13. A process as claimed in claim 10 in which said metal salt comprises at least one salt selected from the group consisting of potassium hydroxide, magnesium hydroxide and copper (I) oxide.

14. A process as claimed in claim 1 in which in step (b) purified carboxylic acid is recovered by fractional distillation with heads and base bleeds and a liquid side draw of purified carboxylic acid.

15. A process as claimed in claim 1 in which steps (a) and (b) are performed together in a distillation column.

* * * * *